United States Patent [19]

Smetana et al.

[11] 4,448,890

[45] May 15, 1984

[54] DETECTION OF HUMAN CANCER CELLS WITH ANTIBODIES TO HUMAN CANCER NUCLEOLAR ANTIGENS

[75] Inventors: Karel Smetana, Prague, Czechoslovakia; Harris Busch; Rose K. Busch; Ferenc Gyorkey; Phyllis Gyorkey; Frances M. Davis, all of Houston, Tex.

[73] Assignee: Baylor College of Medicine, Houston, Tex.

[21] Appl. No.: 191,612

[22] Filed: Sep. 29, 1980

[51] Int. Cl.³ .................... G01N 33/54; G01N 33/58; C07G 7/00
[52] U.S. Cl. ................................ 436/508; 260/112 R; 422/61; 436/547; 436/813; 436/808
[58] Field of Search ...................... 260/112 R, 112 B; 436/508, 547, 813, 808; 422/61

[56] References Cited

U.S. PATENT DOCUMENTS 4,296,201  10/1981  Ax et al. ................................. 435/7

OTHER PUBLICATIONS

Davis et al., Proc. Natl. Acad. Sci. U.S.A., vol. 76, Feb. 1979, pp. 892–896.

Primary Examiner—Christine M. Nucker
Attorney, Agent, or Firm—Fulbright & Jaworski

[57] ABSTRACT

Specific common nucleolar antigens are found in a broad range of human malignant tumor specimens and have been isolated, extracted and purified. Antibodies and antisera specific to these nucleolar antigens are harvested from non-human hosts and used for detection of human cancer cells. Disclosed are (1) methods for isolating the nucleolar antigens, obtaining them in substantially purified form, producing the specific antibodies, obtaining them in substantially purified form, and using the antisera and antibodies induced by the nucleolar antigens in diagnostic procedures for detecting human cancer cells, and (2) diagnostic kits comprising specific antibodies and antisera.

14 Claims, No Drawings

DETECTION OF HUMAN CANCER CELLS WITH ANTIBODIES TO HUMAN CANCER NUCLEOLAR ANTIGENS

FIELD OF THE INVENTION

This invention relates to nucleolar antigen(s) found in a broad range of human cancers and not found in corresponding non-tumor tissues and to antibodies and antisera specific to these nucleolar antigen(s) for diagnostic purposes. BACKGROUND OF THE INVENTION Earlier findings in experimental animals have indicated the presence of nuclear and nucleolar antigens in tumors which were not found in non-tumor tissues (R. K. Busch et al, Cancer Res. 34, 2362, 1974; Yeoman et al, Proc. Natl. Acad. Sci. USA 73, 3258, 1976; Busch and Busch, Tumori 63, 347, 1977; Davis et al, Cancer Res. 38, 1906, 1978; Marashi et al, Cancer Res. 39, 59, 1979). In these early studies by the inventors, antibodies were prepared to nucleoli of rat normal and neoplastic cells by immunization of rabbits (R. K. Busch et al, supra; Busch and Busch, supra; Davis et al, supra). Bright nucleolar fluorescence was demonstrated in the acetone-fixed cells by the indirect immunofluorescence method. It was also found that the immunoprecipitin bands in Ouchterlony gels formed with antisera to Novikoff hepatoma nucleolar antigens extracted from rat Novikoff hepatoma nucleoli differed from the corresponding immunoprecipitin bands produced with liver nucleolar antigens and antiliver nucleolar antisera (Busch and Busch, supra).

Further specificity was shown when antitumor nucleolar antiserum absorbed with liver nuclear extracts produced positive nucleolar fluorescence in Novikoff hepatoma ascites cells but not in liver cells. Conversely, antiliver nucleolar antiserum absorbed with tumor nucleolar extracts did not produce detectable tumor nucleolar fluorescence but did produce positive fluorescence in liver nucleoli (Davis et al, supra).

Inasmuch as immunofluorescence analysis indicated that differences were observable in acetone-fixed tumor smears and normal rat cell smears (particularly after absorption of the antisera with normal liver nuclei and nucleoli), attempts were made to utilize these antisera to rat tumor nucleolar antigens in testing corresponding tissue samples derived from human tumors. Studies with antibodies to rodent tumor nucleoli showed that positive immunofluorescence was not found in human tumor nucleoli. In view of this the present inventors began a new series of experiments to find human nucleolar antigens. Positive immunofluorescence was then found in human tumor tissues with antisera and antibodies to these new human tumor nucleolar preparations. In these studies, the antibodies were absorbed with placental nuclear sonicates as well as fetal calf serum (Busch et al, 39, 3024, 1979; Davis et al, Proc. Natl. Acad. Sci. USA 76, 892, 1979; Smetana et al, Life Sci. 25, 227, 1979).

The present invention has resulted from studies designed to utilize these new human nucleolar antigens for the detection of a broad range of human neoplasms.

The following Table I presents a summary of the human tumors in which a bright nucleolar immunofluorescence was found with the antibodies to human tumor nucleoli. These studies supported the surprising and unexpected discovery that many human tumors contain common nucleolar antigens which exhibits a positive immunofluorescence with antisera or immunoglobulin fractions of such antisera (Busch et al, supra).

TABLE I
BRIGHT NUCLEOLAR IMMUNOFLUORESCENCE IN HUMAN TUMORS (From: Busch et al, 1979)

I. Carcinomas
   1. Bladder, Transitional cell
   2. Brain
      astrocytoma
      glioblastoma
   3. Colon, adenocarcinoma (4)*
      metastasis; liver
      transplantable carcinoma (GW-39)
   4. Eccrine gland, carcinoma
   5. Esophagus, squamous cell carcinoma
   6. Liver, primary carcinoma
   7. Lung:
      adenocarcinoma (2)
      oat cell (2)
      squamous cell (5)
   8. Melanoma, malignant, cerebral metastases
   9. Prostate, adenocarcinoma (4)
   10. Skin: basal cell carcinoma (2)
       squamous cell carcinoma (7)
       metastasis: lymph node
   11. Stomach, adenocarcinoma
       metastasis: liver
       metastasis: lymph node
   12. Thyroid, carcinoma (2)

II Sarcomas
   1. Myoblastoma, malignant of lip
      metastasis to cervical lymph node
   2. Osteogenic sarcoma (3), biopsy, tissue culture
   3. Synovial sarcoma
   4. Lymphoma (4), non Hodgkins III. Hematological Neoplasms
   1. Hodgkins disease (Reed Sternberg, 5)
   2. Leukemia: CLL (5), Hairy cell (spleen)
   3. Lymphoma, lymphocytic, spleen
   4. Multiple myeloma (5)
   5. Mycosis fungoides
   6. Acute myelocytic leukemia (5)
   7. Chronic myelocytic leukemia (5)
   8. Acute monocytic leukemia (2)

IV. Cultures
   1. Breast carcinoma
   2. Colon adenocarcinoma
   3. HeLa
   4. HEp-2
   5. Prostate, carcinoma (3)
   6. Squamous cell carcinoma (3)

*Numbers in parenthesis represent number of cases

In the non-tumor tissues, benign tumors, and inflammatory states, negative results were generally obtained as indicated in the following Table II (Busch et al, supra).

TABLE II
NEGATIVE IMMUNOFLUORESCENCE IN HUMAN TISSUES (From: Busch et al, 1979)

I. Normal Tissue
   1. Bladder
   2. Bone marrow (hemoblastic lines, 5)*
   3. Breast
   4. Buffy coat-blood (3)
   5. Gallbladder
   6. Intestine, small, crypts of Lieberkuhn
   7. Intestine, large
   8. Kidney
   9. Liver (2)
   10. Lung (adjacent to tumor)
   11. Lymph node
   12. Lymphocytes, normal (2)
   13. Pancreas
   14. Pineal gland TABLE II-continued NEGATIVE IMMUNOFLUORESCENCE IN HUMAN
TISSUES (From: Busch et al, 1979)

15. Pituitary
    16. Placenta
    17. Prostate gland
    18. Skin
    19. Stomach
    20. Thyroid gland
II. Benign Growing Tissues
    1. Breast, adenoma
    2. Parathyroid, adenomas (2)
    3. Prostate gland, hyperlasia (3)
    4. Thyroid, adenomas (3)
       nodular goiters (2)
III. Inflammatory Diseases
    1. Chronic ulcerative colitis
    2. Glomerulonephitis
    3. Granuloma and fibrosis of lung
    4. Liver - cirrhosis, hepatitis
    5. Lupus profundus (mammary gland
       and skin)
    6. Pemphigus - bullous
    7. Ulcer, gastric
    8. Inflammatory hyperlasia-lymph nodes (4)
    9. Infectious mononucleosis (5)
IV. Cultures
    1. Breast fibroblasts
    2. Lymphocytes, PHA stimulated

*Numbers in parenthesis represent number of cases

These results, originally obtained with immunofluorescence, have been verified and extended with immunoperoxidase methods.

BACKGROUND REFERENCES

Busch, H., Gyorkey, F., Busch, R. K., Davis, F. M., Gyorkey, P. and Smetana, K. A nucleolar antigen found in a broad range of human malignant tumor specimens. Cancer Res. 39: 3024–3030, 1979.

Busch, R. K. and Busch, H. Antigenic proteins of nucleolar chromatin of Novikoff hepatoma ascites cells. Tumori 63: 347–357, 1977.

Busch, R. K., Daskal, I., Spohn, W. H., Kellermayer, M. and Busch, H. Rabbit antibodies to nucleoli of Novikoff hepatoma and normal liver of the rat. Cancer Res. 34: 2362–2367, 1974.

Dale, G. and Latner, S. L. Isoelectric focusing of serum proteins in acrylamide gels followed by electrophoresis. Clin. Chim. Acta 24: 61–68, 1969.

Davis, F. M., Busch R. K., Yeoman, L. C. and Busch, H. Differences in nucleolar antigens of rat liver and Novikoff hepatoma ascites cells. Cancer Res. 38: 1906–1915, 1978.

Davis, F. M., Gyorkey, F., Busch, R. K. and Busch, H. A nucleolar antigen found in several human tumors but not in nontumor tissues studied. Proc. Natl. Acad. Sci. USA 76: 892–896, 1979.

Garvey, J.S., Cremer, N.E. and Sussdorf, D. H. Methods in Immunology, 1977. W. A. Benjamin, Inc. Reading, Mass.

Hilgers, J., Nowinski, R. C., Geering, G. and Hardy, W. Detection of avian and mammalian oncogenic RNA viruses (oncornaviruses) by immunofluorescence. Cancer Res. 32: 98–106, 1972.

Kendall, F. E. The use of immunochemical methods for the identification and determination of human serum proteins. Cold Spring Harbor Symp. Quant. Biol. 6: 376–384, 1938.

Laurell, C. B. Electroimmunoassay. Scand. J. Clin. Lab. Invest. 29 (Suppl. 124): 21–37, 1972.

Lowry, O. H., Rosebrough, N. J., Farr, A. L. and Randall, R. J. Protein measurement with the Folin phenol reagent. J. Biol. Chem. 193: 265–275, 1951.

Marashi, F., Davis, F. M., Busch, R. K., Savage, H. E. and Busch, H. Purification and partial characterization of nucleolar antigen-1 of the Novikoff hepatoma. Cancer Res. 39: 59–66, 1979.

Smetana, K., Busch, R. K., Hermansky, F. and Busch, H. Nucleolar immunofluorescence in human hematological malignancies. Life Sci. 25: 227–234, 1979.

Tan, E. M. and Lerner, R. A. An immunological study of the fate of nuclear and nucleolar macromolecules during the cell cycle. J. Mol. Biol. 68: 107–114, 1972.

Wallace, R. W., Yu, P. H., Dieckert, J. P. and Dieckert, J. W. Visualization of protein-SDS complexes in polyacrylamide gels by chilling. Anal. Biochem. 61: 86–92, 1974.

Yeoman, L. C., Jordan, J. J., Busch, R. K., Taylor, C. W., Savage, H. and Busch, H. A fetal protein in the chromatin of Novikoff hepatoma and Walker 256 carcinosarcoma tumors that is absent from normal and regenerating rat liver. Proc. Natl. Acad. Sci. USA 73: 3258–3262, 1976.

SUMMARY OF THE INVENTION

The present invention resides in the surprising and unexpected discovery that common nucleolar antigens are found in a broad range of human cancer cells but are not found in normal human cells. The antigens are proteins which may have gene control or other functions and are persistent throughout mitosis in a perichromosomal location. Important aspects of the invention are discovery of the common nucleolar antigens found in human cancer cells, isolation and purification of the nucleolar antigens, production of antibodies specific to these antigens, diagnostic test methods using antibodies specific to these antigens to detect human cancer cells, a diagnostic kit containing either antibodies or antisera specific to these nucleolar antigens.

Accordingly, an object of the present invention is the provision of common nucleolar antigens found in a wide range of human cancer cells.

A further object of the present invention is the provision of antisera and antibodies specific to these common nucleolar antigens which can be used for diagnostic and treatment purposes.

A further object of the present invention is the provision of these nucleolar antigens in substantially purified form.

A further object of the present invention is the provision of processes for extracting and isolating these nucleolar antigens.

A further object of the present invention is the provision of processes for purifying these nucleolar antigens.

A further object of the present invention is the provision of antisera and antibodies having high specificity to common nucleolar antigens found in a broad range of human cancer cells.

A further object of the present invention is the provision of antisera and antibodies induced by and specific to purified antigens found in a broad range of human cancer cells.

A further object of the present invention is the provision of diagnostic kits comprised of antibodies or antisera induced by and specific to nucleolar antigens.

A further object of the present invention is the provision of antisera and antibodies specific to the same antigens found in the nucleoli of a broad range of human cancer cells.

A further object of the present invention is the provision of antibodies and antisera specific to the common or same antigens found in a wide range of human cancer cells which serve as carriers for markers for diagnostic purposes.

Other and further objects, features and advantages of the invention appear throughout.

DESCRIPTION OF THE PREFERRED EMBODIMENTS

The present invention resides in the unexpected and surprising discovery that common specific antigens are present in the nucleoli of a wide range of human cancer cells, their extraction, isolation, and substantial purification, the production of antisera and antibodies of high specificity and selectivity to these nucleolar antigens which can be tagged directly or indirectly to allow diagnostic testing for human cancers in vitro and in vivo.

The Antigen in the Cancer Cells

The antigens have been found in a broad range of human cancers including cancers of the central nervous system, gastrointestinal tract, genitourinary tract, lung, skin, blood forming tissues and endocrine and exocrine glands. For example, the malignant human cells include HeLa cells, prostatic carcinoma, other carcinomas, sarcomas and hematological neoplasms. The antigens can be extracted from nuclei or nucleoli of human malignant cells. The antigens have not been found in corresponding nontumor tissues. In using the diagnostic methods of the present invention to detect malignant cells, approximately one percent false negatives and three percent false positives were detected. The false negatives represent necrotic tumor tissues or non-reactive tumors for reasons unknown. The false positives represent two cases of "preneoplastic tissues" and weak positives in occasional focal regions in "hyperplastic tissue". Two focal positive regions were identified as "preneoplastic regions" or focal neoplastic transformation in gastrointestinal inflammatory tissues.

The antigens have a major species and at least one and possibly more minor antigen species. The major antigen species from human cancer cells (a) has a discrete isoelectric point of from 6.0 to 6.7 and approximately 6.3 as determined by isoelectric focusing, pH 3–10, polyacrylamide gel; (b) has an approximate molecular weight of 50,000 to 60,000 daltons as determined by two-dimensional gel electrophoresis with an SDS(sodium dodecylsulfate) second dimension; (c) is in part tightly bound to nuclear and nucleolar RNP and in part soluble in 0.01 M Tris-HCl, pH 8; (d) and is both nucleolar and extranucleolar but remains "intranuclear" or chromosome-associated during cell division.

The second antigen species which has been detected has a pI of approximately 6.0 (detected by the same procedures as the major antigen species) and its molecular weight is also 50,000 to 60,000 daltons. It is possible that it represents a modified product of the major antigen, but it has not been determined whether it is structurally related. The minor antigen species is in relatively smaller concentration than the major antigen species.

Antigens are also present in nucleolar ribonucleoprotein (RNP) particles obtained by ultracentrifugation of the Tris extracts, subsequently described. The antigen present in these particles is more tightly bound to proteins and ribonucleic acid (RNA) than the antigen in the Tris soluble fraction. It is not yet clear whether the antigens in the RNP particle are identical to those in the supernatant fraction but their isoelectric points are the same and they absorb the antibodies to the antigens. Nucleolar antigens present in fibrils, probably of the nuclear ribonucleoprotein network, are also seen in cancer cells by immune-light microscopy. These are extranucleolar structures which may represent elements from which the RNP particles are derived.

It remains to be determined whether the antigens represent a substance that is present in high concentrations in cancer cells and very low concentrations in noncancerous cells or are fetal antigens as was found earlier in the comparative studies on nuclear antigens of the rat Novikoff hepatoma and normal rat liver cells (Yeoman et al, 1976).

Human Tumors and Other Tissues

All steps for obtaining and analyzing samples of human tissue, blood and serum of suspected cancer patients were approved by the Human Research Committee at Baylor College of Medicine, Houston, Tex. and affiliated hospitals. Sections of human tumors were obtained from frozen sections of surgical specimens, biopsy, or preserved cryostat specimens, mainly from the Department of Pathology from the Houston Veterans Administration Medical Center, and also from The Michigan Cancer Foundation in Detroit, Mich., and the Department of Internal Medicine, Charles University in Prague, Czechoslovakia. These sections were analyzed for the presence of nucleolar antigens by indirect immunofluorescence and immunoperoxidase techniques.

Purification of the Nucleolar Antigens

Purification of the antigens was achieved by extraction of nuclei or nucleoli with 10 mM Tris HCl/0.1 mM PMSF/pH 8 for 6 times in a ratio of 20 volumes to one volume of nuclei or nucleoli. The extract was centrifuged first at 27,000×g for 10 minutes and then at 100,000×g for 16 hours. Ammonium sulfate at 40% saturation was used to remove contaminants. The 40–100% ammonium sulfate fraction was collected by centrifugation and dialyzed against 20 mM Tris HCl/pH 7.6. The antigens were chromatographed on DE-52 cellulose columns (1×10 cm). The antigens were eluted in the 0.15 M NaCl/0.1 mM PMSF/pH 7.6 fraction. Isoelectric focusing gels were used to identify and purify the antigens. These contained 4% acrylamide/8 M urea/2% ampholines (pH 3.5–10). The antigens, pI 6.3 and 6.0 respectively, were cut out of the gels. On SDS (sodium dodecyl sulfate) gels, one major spot was found for each of these antigens.

Preparation of HeLa Cell Nuclei or Nucleoli

HeLa cells were collected from Spinner culture bottles (7–8 liters). The cells should be and were in log phase 7–8×10⁵ cells/ml. The cells were centrifuged at 800×g for 8 minutes to form cell pellets. The cell pellets were suspended in (PBS) phosphate buffered saline (0.15 M NaCl, 0.01 M phosphate, pH 7.2) by gentle homogenization with a loose Teflon pestle and centrifuged at 800×g for 8 minutes. The cells were washed a second time with PBS and the cell pellets were weighed. The cell pellets were suspended by gentle homogenization in 20 volumes of reticulocyte standard buffer (RSB), pH 7.4 and allowed to swell for 30 minutes on ice. The cells were then centrifuged at 1000×g for 8 minutes and resuspended by gentle homogenization in RSB buffer plus 1/20 volume of the detergent Nonidet P40 (10% in RSB). The final volume of Nonidet was 0.5%. The cells were homogenized with a Dounce homogenizer 20-60 strokes until the cells were broken and the nuclei released and freed of cytoplasm. The cells were then centrifuged $1000 \times g$ for 8 minutes, resuspended by gentle homogenization in 0.88 M sucrose, 0.5 mM Mg acetate ($20 \times$ weight-volume) and centrifuged at $1500 \times g$ for 20 minutes. The resulting pellet contained the HeLa nuclei that were used to prepare the antigen extracts described below. Nuclei from other human malignant cells may be obtained in a similar manner.

For isolation of nucleoli, the nuclear pellet as prepared above was next suspended by gentle homogenization in 0.34 M sucrose, 0.5 mM Mg acetate using 2 ml of sucrose for each gram of original cells. The nuclei were sonicated (with a Branson sonifier) by 10-second bursts (and 10 seconds rest). Total time was between 60 and 110 seconds. The nucleoli released were monitored by microscopic examination. To visualize the nucleoli, they were stained with Azure C (the solution consists of 1% Azure C in 0.25 M sucrose). The preparation should be free of nuclei at the end of the sonication period. The sonicated fraction was underlayed with three times the volume of 0.88 M sucrose (without Mg acetate) and centrifuged $1500 \times g$ for 20 minutes. The resulting pellet contained the HeLa nucleoli which may be used as the immunogen.

Satisfactory purification has usually resulted with the above procedure (Busch and Smetana, 1970), and light microscopy showed the quality of these preparations was essentially satisfactory. However, electron microscopic analysis indicated the presence of chromatin and nuclear contaminants. The key problem in adequate purification of these preparations is the limited amount of original HeLa cells in the cultures which limit the number of repurification steps. Nucleoli prepared from 5- to 10-g HeLa cell preparations, rather than the 0.5- to 1-g quantities used in earlier studies, provided sufficient material for adequate purification. The conditions for growing the HeLa cells and the isolation of placental nuclei were essentially the same as those reported previously (Davis et al, 1979).

Preparation of the HeLa Tris Extract

The HeLa nuclei were suspended in NaCl-EDTA buffer $10 \times$ weight/volume, 1 g nuclei/10 ml buffer. (Buffer: 0.075 M NaCl, 0.025 M Na EDTA/pH 8, 1 mM PMSF) The phenylmethylsulfonylfluoride (PMSF) is made up at 100 mM concentration in isopropyl alcohol. It is added to each solution prior to the extraction. The suspension was homogenized with a Dounce homogenizer 20 strokes and centrifuged at $3000 \times g$ for 5 minutes. Supernatant was collected. The above extractions were repeated on the nuclear pellet two more times. The NaCl-EDTA extract was not used in the present antigen work; therefore, it was discarded. The nuclear pellet was suspended in $10 \times$ weight/volume 0.01 M Tris-HCl; pH 8, 1 mM PMSF and homogenized with a Dounce homogenizer for 20 strokes, although 0.01 M Tris-HCl pH 7-9 is satisfactory. The supernatant was collected and saved on ice. During the Tris extractions, the nuclei broke and chromatin was released. The nuclear breakage was monitored by microscopic examination. The pellet was resuspended in the Tris buffer and the nuclei were allowed to "swell" for 15 minutes on ice. It was then "Dounce" homogenized for 20 strokes and centrifuged at $12,000 \times g$ for 10 minutes. The supernatant was saved. The pellet was resuspended and had a whitish fluffy appearance. It was again "Dounce" homogenized for 20 strokes and centrifuged at $27,000 \times g$ for 30 minutes. The supernatant was collected and combined with previous supernatants from the Tris extracts.

The Tris extracts were then concentrated with an Amicon UM-10 or PM-10 Diaflo membrane. Generally, the volume at the beginning is around 50 ml and this was concentrated to 4-5 ml. The final concentration of protein is around 4-5 mg/ml. The rabbit may be immunized with this Tris extract.

By following the above procedure, extracts may also be prepared from HeLa nucleoli and from nuclei or nucleoli of other human malignant cells.

For the Tris immunogen, dilute 250 $\mu$l of Tris extract (4-5 mg/ml) as prepared above with 250 $\mu$l PBS. Combine this with the Freund's adjuvant as described for the nucleolar immunogen below.

Immunization of Rabbits with HeLa Cell Nucleolar Preparations to Produce Antibodies The HeLa nucleoli were weighed (20-30 mg, wet weight) and suspended evenly in 0.5 ml 0.01 M phosphate buffered saline, pH 7.2. They were then mixed with 0.6 ml Freund's complete adjuvant (GIBCO) as follows: The suspended nucleoli were placed in a 5 ml syringe and the Freund's adjuvant in a second syringe. To each syringe an 18 gauge needle from which the tip had been removed was attached. The needles were then connected by a piece of polyethylene tubing, I.D. 0.047 (Clay-Adams). The contents of the syringes were mixed until the preparation became thickened and was difficult to force through the tubing.

The rabbit was shaved on the back and injected intradermally at 6 sites, 0.1 ml/site. The remaining 0.4-0.5 ml was injected, half subcutaneously (under the loose skin on the upper back) and half intramuscularly (in the thigh muscle). The injections were given once a week for three weeks with similar amounts of nucleoli each time. The first bleeding was carried out 7-10 days after the third week of immunization. A rabbit ear cup (Bellco) and a vacuum pump were used to collect the blood. The blood (approximately 45-50 ml) was allowed to clot for 3-4 hours at room temperature. The serum portion was removed from the tube and centrifuged at 1000 g for 30 minutes (this sediments any free red blood cells). The clear serum was collected and was then absorbed (or kept frozen until ready for the absorption procedure). The blood clot may be refrigerated overnight. This releases a few additional ml of serum. The serum from each bleeding was assayed for the presence of nucleolar antibodies by the indirect immunofluorescence procedure.

Other non-human hosts (e.g. goat, sheep, horse, chicken, etc.) may be immunized with human malignant cell nucleoli preparations to elicit the antisera or antibodies to the nucleolar antigen(s) of the present invention. Antisera may also be prepared by immunization of non-human hosts animals with extracts (e.g. tris extract) of human malignant cell nuclei or nucleoli.

Absorption of Antinucleolar Antiserum

The rabbit antiserum was first absorbed with 20% normal human serum and 20% fetal calf serum (GIBCO). 20% normal human serum was added to the rabbit antiserum (4 ml/20 ml) and incubated for 1 hour in a 37° C. shaking water bath. The flask was removed, 20% fetal calf serum (4.8 ml/24 ml) was added, and incubation was carried out for 1 hour in a 37° shaking water bath. The flask was removed and incubated an additional hour at room temperature with mixing by gentle swirling every 15 minutes. It was then centrifuged at 15,000×g for 30 minutes, and the supernatant (absorbed serum) was removed and saved. The absorbed serum was converted to the immunoglobulin (Ig) form by following the procedure given for the $(NH_4)_2SO_4$ precipitation of serum, subsequently described.

The Ig preparation from the nucleolar antiserum which had been absorbed with normal human serum and fetal calf serum was now absorbed with a normal human tissue (placenta or liver). An equal volume of placental nuclear sonicate in PBS 7.2 (10–15 mg protein/ml) was added to the absorbed nucleolar immunoglobulin (10 ml Ig plus 10 ml nuclear sonicate) and incubated for 1 hour in a 37° C. shaking water bath. It was then incubated for an additional hour at room temperature with mixing by gentle swirling of the flask every 15 minutes and then centrifuged at 15,000×g for 30 minutes. The supernatant was collected and the absorbed Ig was reprecipitated with $(NH_4)_2SO_4$ as described. This Ig can be used as the final antibody product or it can be further purified by diethylaminoethyl (DEAE) cellulose chromatography as follows:

The Ig which is contained in the 0.01 M phosphate buffered saline pH 7.2, is dialyzed against 0.0175 M phosphate buffer pH 6.3 (without saline). After dialysis, it is centrifuged at 2500×g for 20 minutes. The supernatant is added to the DEAE column (20 mg of protein per gram of cellulose, Whatman DE52). The IgG is eluted from the column with the 0.0175 M phospate buffer. After elution, the IgG fraction is dialyzed against the 0.01 M phosphate buffered saline pH 7.2.

The same procedure was followed for the control serum which consisted of preimmune serum which was obtained by bleeding the rabbit (or other non-human host animal) before the immunization was started.

Preparation of Rabbit Immunoglobulin Ig

A saturated $(NH_4)_2SO_4$ solution (760 gm/liter) was prepared and an equal volume of cold saturated $(NH_4)_2SO_4$ was added drop by drop to the antiserum with stirring. A white precipitate formed and the precipitate was allowed to aggregate for 1 ½–2 hours on a magnetic stirrer in the cold. The precipitated antiserum was centrifuged at 3000×g for 20 minutes. The supernatant was removed and the pellet was resuspended in PBS, pH 7.2 (approximately half the volume of the original serum). The solubilized pellet was placed in a dialysis bag and dialyzed against 100 volumes of PBS overnight in the cold (with magnetic stirring). The dialysis bag was placed in fresh PBS (100×volume) the following morning and dialysis was continued for 6 hours. The immunoglobulin was carefully removed from the dialysis bag and centrifuged at 2500×g for 20 minutes. The supernatant was collected.

Immunofluorescence

The procedure described earlier (RK Busch et al, 1974; Hilgers et al, 1972) for immunofluorescence was used in this study, as follows:

Indirect Immunofluorescence Method:

150 µl of antinucleolar antiserum diluted 1:50 was placed on acetone fixed HeLa cells or on fixed tissue specimens (from Hilgers et al, 1972; RK Busch et al, 1974). It may be necessary to use more than 150 µl if the tissue specimen covers a large section of the slide. Dilution of antiserum (As) is dependent on antibody (Ab) titer. Other dilutions can be used up to the point where As or Ab dilutions become too dilute to yield positive response to known positive cells (e.g. HeLa). The slides were incubated in a moist chamber for 45–50 minutes at 37° C. (The moist chamber may consists of a large petri dish to which has been added a moist paper towel.) After the incubation, the antiserum was washed off the slide by the gentle addition of PBS and the slides were placed in a slide holder and washed in PBS for 1 hour. The PBS was changed three times, at 15 minutes, 30 minutes and 45 minutes. The slides were removed from PBS and dipped in distilled or deionized water ten times with rapid up and down movements. The slides were dried with cold air from a blow or hair dryer (2–3 minutes), being careful not to overdry. 150 µl of fluorescein labeled goat antirabbit antiserum (Hyland or Cappel) diluted 1:10 was placed on the slides and incubated in the moist chamber for 30–35 minutes at room temperature. The second antibody was removed from the slide by a gentle PBS wash. The slides were then washed in PBS for 1 hour with three changes, at 15 minutes, 30 minutes and 45 minutes; or after the first 15 minutes wash, they can be placed in fresh PBS and left in the refrigerator overnight. After the final wash with PBS, the slides were dipped in deionized or distilled water ten times with rapid up and down movements and dried with cold air from a blow or hair dryer (2–3 minutes). A solution of glycerol and PBS in a 1:1 ratio was added to the cells or tissue specimen and covered with a cover slip. The specimen can be preserved for several months if the cover slip is sealed with a sealant, such as clear nail polish and kept cold. The slide was then examined with a fluorescence microscope. Nucleolar fluorescence was not observed with preimmune immunoglobulin or preimmune IgG fractions. The other immunological techniques used were the same as those used in earlier studies (Kendall, 1938; Lowry et al, 1951; Dale and Latner, 1969; Laurell, 1972; Wallace et al, 1974; Marashi et al, 1979). For analysis of nucleolar localization of immunofluorescence, samples were switched in and out of phase contract illumination during fluorescence observation.

Immunoperoxidase Method

Instead of fluorescein-labeled goat antirabbit 150 µl of peroxidase labeled goat antirabbit 1:10 or 1:20 dilution was added. Localized peroxidase activity can be demonstrated by a number of redox dye systems for light or electron microscopic examination. Other enzymes can serve as labels for the indirect method and peroxidase and other enzymes can be used directly by labeling the primary antibody.

Prepare Karnofsky's incubation medium as follows: weigh out enough diaminobenzidine (Sigma) and suspend in 0.05 M Tris-HCl, pH 7.6 so that the concentration is 0.5 mg/ml. Prepare a hydrogen peroxide solution of 0.02% (in the 0.05 M Tris-HCl buffer). Mix the 0.5 mg/ml DAB and the 0.02% $H_2O_2$ in equal proportions a 1:1 ratio (this solution was freshly prepared each time it was used and was kept cold during the preparation).

Add 200-300 μl of the DAB and H$_2$O$_2$ mixture to the slide and incubate for 30 minutes in a moist chamber at room temperature.

After this incubation, remove the DAB and H$_2$O mixture by washing the slide with the 0.05 M Tris HCl pH 7.6 buffer to which has been added 0.1 M NaCl. The slides are given two 10 minutes washes in 0.05 M Tris HCl pH 7.6 0.1 M NaCl. Finish processing of slides as indicated in Steps 11-14 (except the PBS has been changed to Tris HCl). The completed slide is examined by light microscopy.

Preparation of HeLa Cell Slides for Immunofluorescence

A stock supply of fixed HeLa cells was prepared as follows: Actively growing cells from the HeLa culture bottle were removed and washed one time with PBS, pH 7.2. The cells were suspended so that there were at least 1.5×10$^6$ cells/ml. One drop of the HeLa cell suspension was placed on each washed slide (cleaned with detergent, rinsed with distilled or deionized water, cleaned with alcohol, rinsed and dried with heated air from hair dryer) and spread slightly and allowed to dry at room temperature (or in the cold overnight). The dried cells were fixed by placing the slides at 4° C. in acetone for 12 minutes. The slides were numbered with a diamond point glass marking pencil. The slides were used as positive controls for immunofluorescence.

Malignant Tumors as Detected with the Test Antibody

The present studies confirm that nucleolar antigens are present in tumor cells but are not found in nontumor tissues Initial studies demonstrated that, both in cell cultures in human tumors and in specimens from either autopsy or biopsy samples, bright nucleolar fluorescence was produced by the double antibody technique (indirect immunofluorescence), and a corresponding result was not obtained with a series of nontumor tissues (Davis et al, 1979). In later studies, more than 60 malignant tumors were studied and a variety of tissue controls were also evaluated. It is of much interest that this broad array of malignant tumors of ectodermal, endodermal, and mesodermal origin exhibited the presence of one or more common nucleolar antigens (Table I).

EXAMPLE 1

Normal Tissues—In 17 nontumor tissues there was no nucleolar fluorescence following incubation of the antisera or antibodies with the various fixed cell preparations. It was of particular interest that neither the Malpighian layer of the skin, nor the cells of the bone marrow, nor the crypts of Lieberkuhn demonstrated positive immunofluorescence with this procedure. Moreover, the variety of nontumor tissues adjacent to the neoplasms were also negative; these include many tissues of varying types. A group of benign tumors evaluated, including several types of thyroid adenomas, were also negative (Table II).

EXAMPLE 2

Inflammatory Lesions—To ascertain whether an inflammatory response was related to the appearance of these antigen(s), studies were made on 8 types of inflammatory tissues. In most of these, there was no notable fluorescence in the nucleoli of the cells studied. However, sections were found in the ulcerative colitis and gastric ulcer specimens which did exhibit positive nucleolar fluorescence. Notably, 2 of 3 sections of the ulcerative colitis were negative and one showed definite positive nucleolar fluorescence. In the gastric ulcer, one of the 2 sections analyzed exhibited positive nucleolar fluorescence. These results are particularly interesting in view of the known propensity of these lesions to undergo malignant change. It was of special interest to review both the focal positive and negative regions of these slides in the hematoxylin eosin-stained sections; these showed that there were indeed regions in these lesions which exhibited not only mitotic figures but also a heaping up of the epithelial lining. This finding suggested that these cells might constitute preneoplastic lesions or carcinoma in situ. It is possible that the finding of these fluorescent regions might aid in decisions to proceed surgically with either local or more general resections of the affected lesions.

EXAMPLE 3

Artifacts—In the gastric epithelium, there was a region of fluorescence in each cell which was non-nucleolar that appeared to represent a nonspecific localization of the fluorescent antibody. In a crypt of the small intestine, a nonspecific localization of the antibody appeared to occur in the form of aggregates; in most instances, prefiltration of the antibodies through a 0.45 μm Millipore filter eliminated these aggregates. In a sample of breast tissue, which was negative for nucleolar fluorescence, small nonspecific immunofluorescent specks were generally distributed with no special localizing features with regard to cell morphology. The diameters of these very small nonspecific precipitates were 0.5 to 0.1 μm as compared to the nucleolar diameters in the nuclei and nucleoli which were 4 to 6 μm.

EXAMPLE 4

Fluorescence during Phases of the Cell Cycle—The nucleolar fluorescence was readily visualized in the interphase nucleoli. In metaphase, the nucleolar fluorescence was not seen as a distinct entity but was visible between the chromosomes and in the junctional area between the "nucleus" and the cytoplasm. Inasmuch as the nucleolus largely disappears during metaphase and rRNA synthesis ceases in late prophase, it was not surprising that the nucleolar fluorescence was not visible as a distinct entity in such cells (Tan and Lerner, 1972). However, the finding that remnants of the immunofluorescent products persist throughout mitosis suggests that the nucleolar substructures (rather than the nucleolar products) contain the antigens which are persistent epigenetically.

EXAMPLE 5

Malignant Tumor Negatives—In the series of malignant tumors, negative regions were found in varying extents throughout the slides. In general, these correlated with either necrotic or abscessed portions of the neoplasms. In one sample of a tumor of the brain, the mass which exhibited no positive fluorescence was necrotic; many leukocytes were present but there was no defined structure. One adenocarcinoma, which metastasized to the brain, did not exhibit positive fluorescence; the reasons were not clear. Inasmuch as 61 of 63 tumors studied had positive nucleolar fluorescence, 97% of the series studied was positive. These studies now have been broadly extended to over 300 human cancer specimens including a series of cancers of the breast, prostate, lung and hematological tumors with very similar results.

EXAMPLE 6

Labeling—Direct immunochemical methods for the demonstration of the antibodies include labeling the primary antibody with one or more of the following labels: a radioisotope for autoradiography such as $^{125}I$, $^{131}I$, $^{14}C$, or $^{3}H$; a fluorescent dye such as fluorescein or tetramethyl rhodamine for fluorescence microscopy, an enzyme which produces a fluorescent or colored product for detection by fluorescence or light microscopy, or which produces an electron dense product for demonstration by electron microscopy; or an electron dense molecule such as ferritin for direct electron microscopic visualization.

Indirect immunochemical methods include labelling the second antibody or other binding protein specific for the first antibody with a fluorescent dye, an electron dense compound, an enzyme which produces a product detectable by light, flourescence or electron microscopic examination or a radioisotope detectable by autoradiography.

The indirect immunochemical methods for the visualization of the antibodies include application of hybrid primary or secondary antibodies or antibody fragments (F(ab')$_2$) wherein part of the hybrid antibody preparation is specific for the nucleolar antigens, (hybrid primary antibody) or for the primary antibody (hybrid second antibody), and part is specific for a label, such as those mentioned in the preceeding paragraph.

Diagnostic Kits

Labelled conjugated and nonconjugated antibodies may be packaged separately in phosphate buffered saline (PBS) or other buffered suspending agents for distribution. Suitable suspending agents include glycerin, heparin, or sucrose. Suitable buffers include barbital buffers, morpholine buffers, MOPS-3-(N-morpholino) propane sulfonic acid, hepes-N-2-hydroxyethylpiperazine-N-2-ethane sulfonic acid, Tris carbonate and the like.

The present invention, therefore, is well suited and adapted to attain the objects and ends and has the features mentioned as well as others inherent therein.

While presently preferred embodiments of the invention have been given for purposes of the disclosure, changes can be made therein within the spirit of the invention as defined by the scope of the appended claims.

What is claimed is:

1. Antigens selected from the group consisting of isolated nucleoli and nuclear extracts which contain nucleoli constituents, the antigens being in substantially purified form and having major and minor species, the major species having the following characteristics,
   a pI on isoelectric focusing of about 6.0 to 6.7, and
   a molecular weight of about 50,000 to about 60,000 daltons,
   is soluble in 0.01 M Tris HCl pH 8, and
   is primarily localized in nucleoli of human cancer cells.

2. Antigens selected from the group consisting of isolated nucleoli and nuclear extracts which contain nucleoli constituents, the antigens having major and minor species, the major species having the following characteristics,
   a pI on isoelectric focusing of about 6.0 to 6.7, and
   a molecular weight of about 50,000 to about 60,000 daltons,
   is soluble in 0.01 M Tris HCl pH 8,
   is primarily localized in nucleoli of human cancer cells, and
   is substantially purified by sequential purification by ammonium sulfate precipitation, DEAE-column chromatography, Sephadex gel exclusion, cation exchange and calcium phosphate gel chromatography, and preparative isoelectric focusing.

3. A diagnostic kit comprising,
   antibodies characterized by specificity against human cell associated nucleolar antigens in substantially purified form having major and minor species, the major species having the following characteristics,
   a pI on isoelectric focusing of about 6.0 to 6.7, and
   a molecular weight of about 50,000 to about 60,000 daltons,
   is soluble in 0.01 M Tris HCl pH 8, and
   is primarily localized in nucleoli of human cancer cells,
   the antibodies having a label detectable by one of light, fluorescence, electron microscopy, indirect assay methods and autoradiography, and
   disposed in a buffered suspending agent or solution.

4. A diagnostic kit containing,
   antibodies characterized by specificity against antigens selected from the group consisting of isolated nucleoli and nuclear extracts which contain nucleoli constituents, the antigens being in substantially purified form and having major an minor species, the major species having the following characteristics,
   a pI on isoelectric focusing of about 6.0 to 6.7, and
   a molecular weight of about 50,000 to about 60,000 daltons,
   is soluble in 0.01 M Tris HCl pH 8, and
   is primarily localized in nucleoli of human cancer cells,
   the primary antibodies being unlabeled and in a buffered suspended agent or solution, and
   appropriate labeled or unlabeled reagents for detection of the primary antibodies in fixed human malignant cells by a method selected from the group consisting of live micrscopy, fluorescent microscopy, electron microscopy and autoradiography.

5. A process for the immunological detection of cancer in human tissue sections, smears and exfoliative cytological preparations comprising,
   contacting specimens with the antibodies of claims 3 or 4, and
   demonstrating the localization of said antibodies in the nucleoli of malignant calles but not normal cells.

6. The process of claim 5 wherein,
   the antibodies are elicited to nucleoli isolated from one of the family of malignant human cells consisting of HeLa cells, carcinomas, sarcomas, and hematological neoplasms.

7. The process of claim 5 wherein,
   the antibodies are elicited to nucleoli isolated from one of the group consisting of HeLa cells or human prostatic carcinoma cells.

8. The process of claim 5 wherein,
   the antibodies are elicited to extracts of nuclei or nucleoli of malignant human cells from the family consisting of HeLa cells, carcinomas, sarcomas, and hematological neoplasms.

9. The process of claim 5 wherein, the antibodies are elicited to extracts of nuclei or nucleoli of one of the group consisting of HeLa cells or human prostatic carcinoma cells.

10. The process of claim 5 wherein,
the antibodies are elicited to extracts of nuclei or nucleoli of malignant human cells obtained by extraction of 0.01 M Tris HCl, pH 7–9.

11. The process of claim 5 wherein,
the immunological detection of cancer is by indirect immunochemical demonstration of the antibodies of claim 4.

12. A method of purifying nucleolar antigens comprising, sequential purification thereof by ammonium sulfate precipitation, DEAE-column chromatography, Sephadex gel exclusion, cation exchange and calcium phosphate gel chromatography, and preparative isoelectric focusing.

13. The process of claim 12 where,
the nucleolar antigens are extracted from nuclei or nucleoli from human cancer cells.

14. A process of preparing antibodies with specificity against antigens found in nucleoli of human cancer cells comprising,
immunizing a non-human host animal with the antigens of claims 1 or 2, and
harvesting the antibodies of the immunized animal.

* * * * *

UNITED STATES PATENT OFFICE
CERTIFICATE OF CORRECTION

Patent No. 4,448,890     Dated May 15, 1984

Inventor(s) Karel Smetana, et al.

It is certified that error appears in the above-identified patent and that said Letters Patent are hereby corrected as shown below:

Column 10, line 13, change "consists" to --consist--.

Column 14, line 29, change "an" to --and--.

Column 14, line 43, change "micrscopy," to --microscopy,--.

Column 14, line 51, change "calles" to --cells--.

Signed and Sealed this

Ninth Day of October 1984

[SEAL]

Attest:

Attesting Officer

GERALD J. MOSSINGHOFF

Commissioner of Patents and Trademarks